(12) United States Patent
DiBianca

(10) Patent No.: US 6,335,957 B1
(45) Date of Patent: Jan. 1, 2002

(54) VARIABLE RESOLUTION IMAGING SYSTEM

(75) Inventor: Frank A. DiBianca, Memphis, TN (US)

(73) Assignee: The University of Tennessee Research Center, Knoxville, TN (US)

( * ) Notice: Subject to any disclaimer, the term of this patent is extended or adjusted under 35 U.S.C. 154(b) by 0 days.

(21) Appl. No.: 09/228,870

(22) Filed: Jan. 12, 1999

(51) Int. Cl.⁷ .............................................. G01N 23/00
(52) U.S. Cl. ........................................ 378/19; 378/98.8
(58) Field of Search .................................. 378/19, 98.8

(56) References Cited

U.S. PATENT DOCUMENTS

| | | | |
|---|---|---|---|
| 4,029,963 A | * 6/1977 | Alvarez et al. ................. 378/5 |
| 4,057,725 A | * 11/1977 | Wagner ........................ 378/19 |
| 4,262,202 A | 4/1981 | Cusano et al. | |
| 4,415,808 A | 11/1983 | Cusano et al. | |
| 4,417,354 A | * 11/1983 | Pfeiler .......................... 378/19 |
| 4,651,005 A | 3/1987 | Baba et al. | |
| 5,040,199 A | 8/1991 | Stein | |
| 5,270,923 A | 12/1993 | King et al. | |
| 5,533,080 A | 7/1996 | Pelc | |
| 5,781,606 A | * 7/1998 | Dobbs et al. .................. 378/19 |

* cited by examiner

Primary Examiner—Craig E. Church
(74) Attorney, Agent, or Firm—Pillsbury Winthrop LLP

(57) ABSTRACT

This invention relates to an imaging system useful in medical and industrial x-ray imaging, including classical and digital radiography, and classical CT scanning. The imaging system of the present invention provides an increased spatial resolution over imaging systems of the prior art by angulating an x-ray detector or detector array with respect to a radiation source.

31 Claims, 9 Drawing Sheets

VARIABLE RESOLUTION IMAGING SYSTEM

BACKGROUND OF THE INVENTION

1. Field of the Invention

This invention relates to an imaging system useful in medical and industrial x-ray imaging, including classical and digital radiography, and CT scanning. The imaging system of the present invention provides an increased spatial resolution over imaging systems of the prior art by angulating an x-ray detector or detector array with respect to a radiation source.

2. Description of the Prior Art

A number of prior art systems and devices exist for x-ray imaging. The resolution of prior art imaging systems is limited by a variety of different factors. In conventional x-ray detectors, resolution limitations arise from the ranges of electrons and reabsorbed, scattered x-ray photons released in the x-ray detection media.

In imaging systems which use x-ray intensifying screens and in image intensifiers, further resolution limitations arise from lateral light propagation in the detection media. In clear intensifying screen plus lens imaging systems, resolution limitations arise from optical aberrations which depend upon the x-ray absorption position.

In discrete scintillator plus photodetector systems, resolution limitations arise from finite cell dimensions. In gas ionization detectors, resolution limitations arise from finite cell or electrode size and from effects which disperse the ion positions during collection.

The apparatus of the present invention provides significantly improved resolution over x-ray imaging systems of the prior art. The x-ray imaging system of the present invention further provides information on the energy of detected photons. Such information is useful in differentiating component tissues and other materials in the subject based, not only on, gross x-ray absorption, but also on absorption vs. photon energy. The energy discriminating capabilities of the present system provide information allowing isolation of subject components according to atomic number, thereby allowing for chemical identification of components such as calcium, water, fat, and any contrast agents used.

SUMMARY OF THE INVENTION

The present invention is directed toward an imaging system for providing an image of a target body. The invention comprises a radiation source capable of emitting a beam of electromagnetic radiation. The source is aimed at a target body. Depending upon the size of the target body, the invention may also comprise a collimator positioned between the radiation source and a target body so as to control the lateral dimension of the beam within a preselected range.

The invention further comprises a linear first detector array comprising a multiplicity of detectors. The detector array may comprise a multiplicity of scintillator crystals and photodiodes. Alternatively, the detector may comprise a continuous detection medium. The first detector array is oriented such that a radiation beam from a radiation source strikes the detector array at a tilt angle sufficient to define a field of view of sufficient size to image a target body. Because of the angulation of the detector array, the detector cells appear closer in projection as viewed from the radiation source, thereby proportionately increasing the spatial resolution. The detector array is capable of generating a signal indicative of integrated or counting data.

The invention further comprises a signal receiving and storage device connected to receive a signal indicative of integrated or counting data. The signal receiving and storage device is further capable of storing integrated or counting data from the detector array.

The invention further comprises an image display system coupled to the receiving and storage device and capable of displaying images derived from integrated or counting data in the receiving and storage device.

DESCRIPTION OF THE PREFERRED EMBODIMENTS

Figure 1:
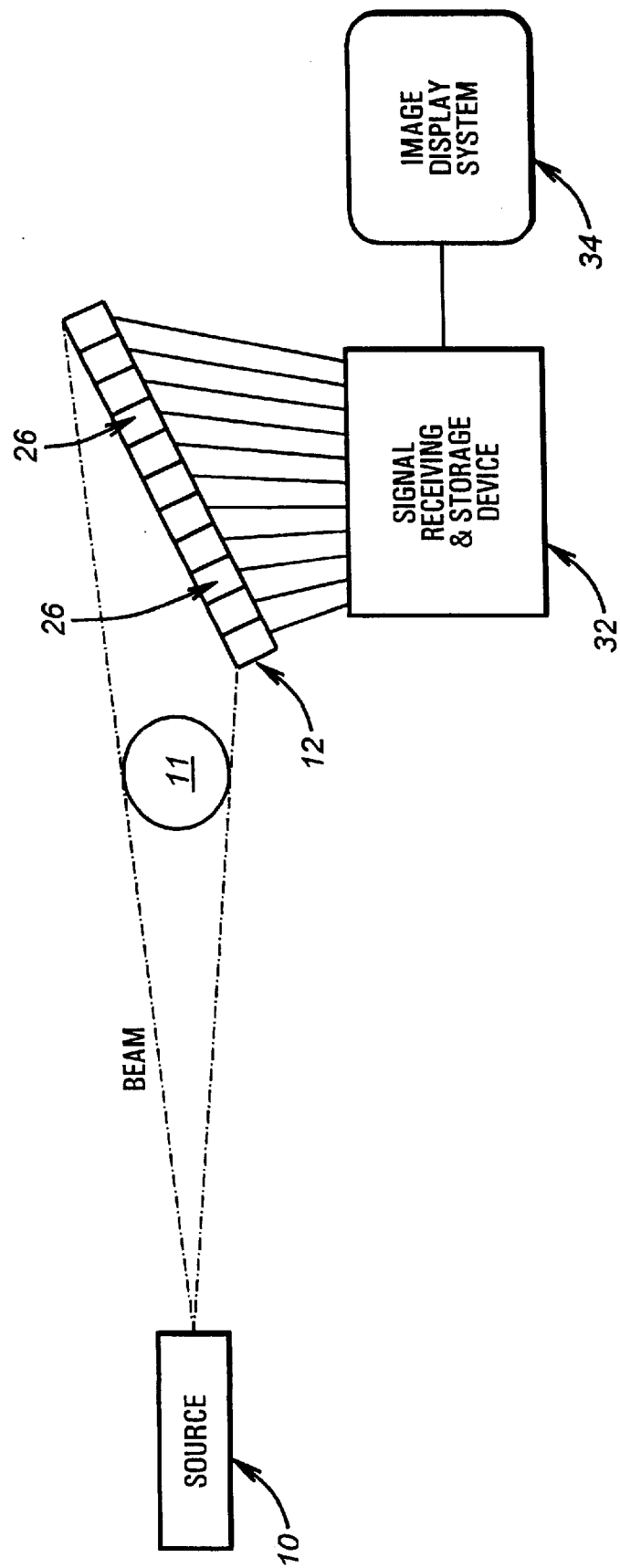
FIG. 1 is a top view of a first embodiment of the present invention.

A first embodiment of the present invention is shown in FIG. 1. This embodiment comprises a radiation source 10 capable of emitting a beam of electromagnetic radiation. In a preferred embodiment the electromagnetic radiation may be x-rays. The source is aimed at a target body 11.

This embodiment further comprises a linear first detector array 12 comprising a multiplicity of detector cells 26. The first detector array is oriented such that the radiation beam strikes the detector array at a tilt angle sufficient to define a field of view of sufficient size to image a target body. The first detector array is capable of generating a signal indicative of integrated or accounting data. In a preferred embodiment each detector cell in the first detector array comprises a scintillator crystal 73 and photomultiplier tube 74 as shown in FIG. 7.

This embodiment of the invention further comprises a signal receiving and storage device 32 connected to receive a signal indicative of integrated or counting data and to store the integrated or counting data from the detector array. This embodiment further comprises an image display system 34 coupled to the receiving and storage device. The image display system is capable of displaying images derived from integrated or counting data stored in the signal receiving and storage device.

Figure 2:
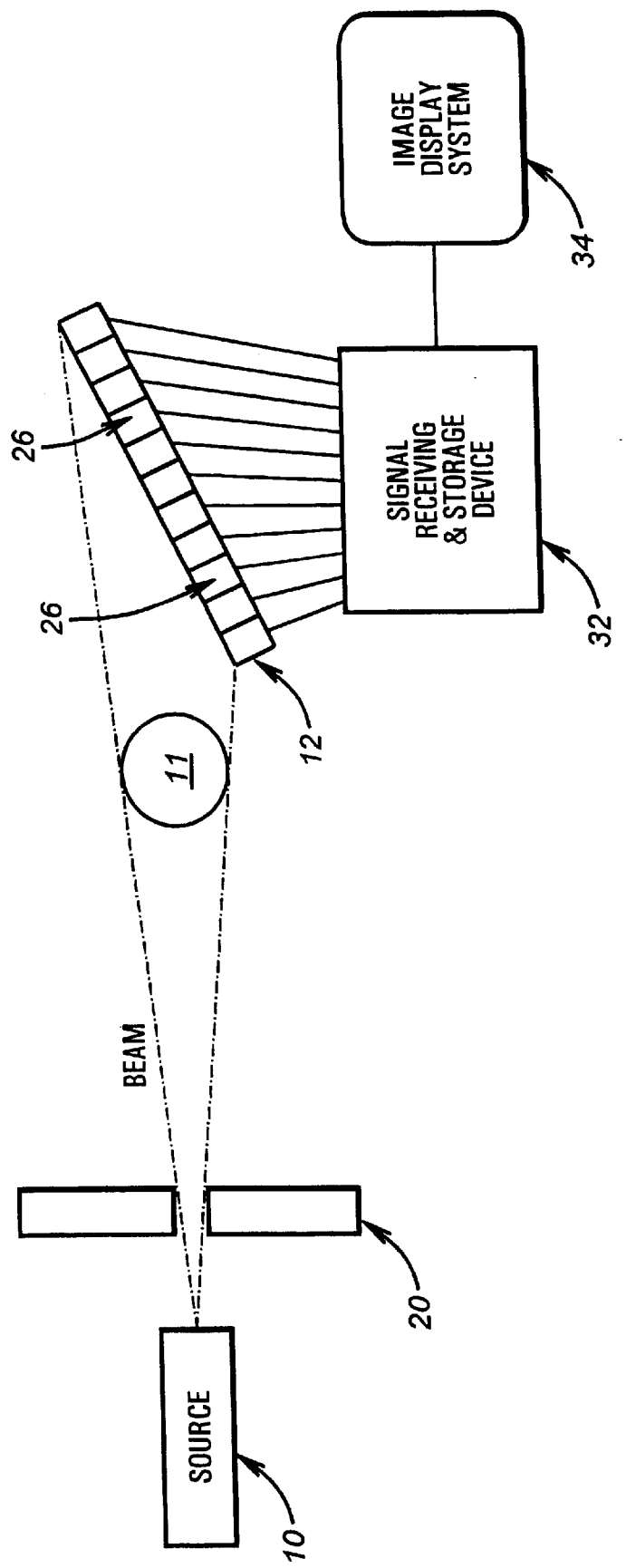
FIG. 2 is a top view of a second embodiment of the present invention.

A second embodiment of the present invention is shown in FIG. 2. This embodiment of the invention further comprises a collimator 20 positioned between the radiation source 10 and the target body 11 so as to control the lateral dimension of the beam within a preselected range, as shown in FIG. 2.

Figure 7:
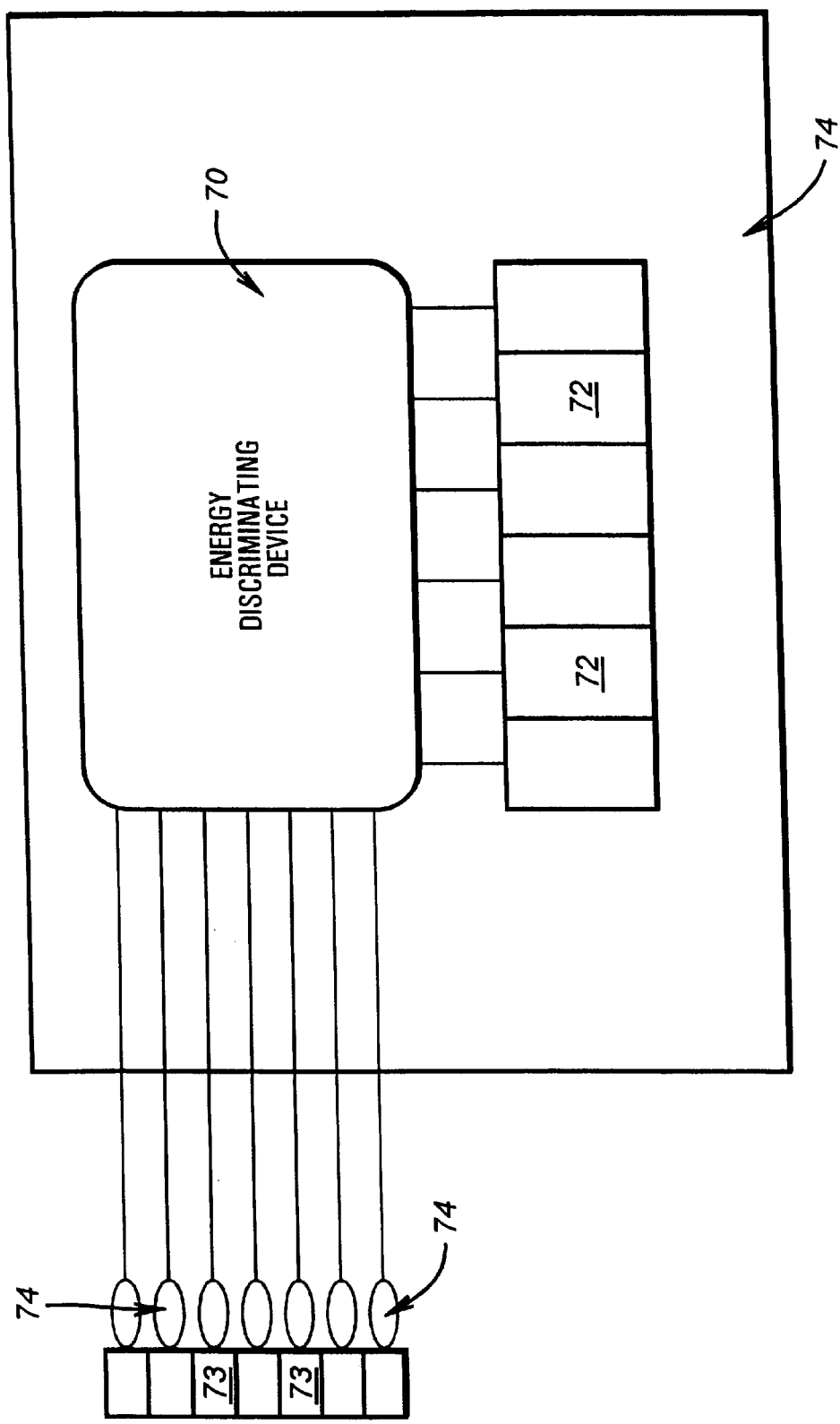
FIG. 7 is a block diagram of a signal receiving and storage device of the present invention.

In a preferred embodiment, the signal receiving and storage device further comprises an energy discriminating device 70 and a multiplicity of bins 72 such that the received signals can be stored according to their energy level, as shown in FIG. 7. One example of an energy discriminating device suitable for use in the present invention is a pulse height analyzer.

Figure 6:
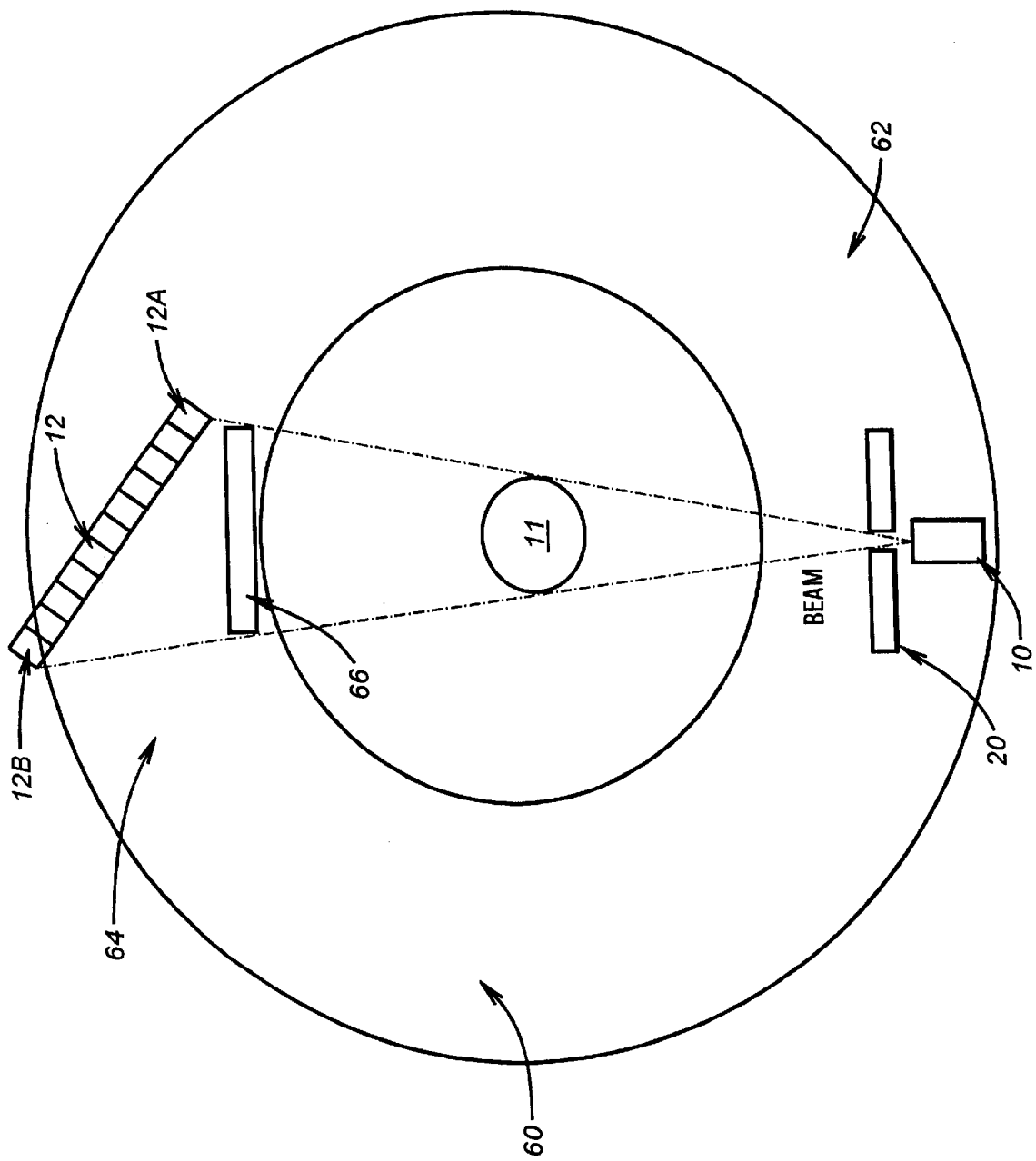
FIG. 6 is a top view of the rotatable gantry of the present invention.

In a preferred embodiment, the invention further comprises a rotatable gantry 60 having a first side 62 affixed to the radiation source and the collimator, as shown in FIG. 6. The rotatable gantry further has a second side 64 affixed to the detector, as shown in FIG. 6. In a preferred embodiment, an antiscatter collimator 66 is affixed to the second side of the gantry and positioned between the detector array and the radiation source, as shown in FIG. 6.

This second embodiment of the invention further comprises a first detector array 12 comprising a proximal end 12a and a distal end 12b. The proximal end is closer to the radiation source then the distal end. The first detector array is oriented such that a radiation beam strikes it at an angle within the range of 0.0005–90 degrees. The first detector array is capable of generating a signal indicative of integrated or counting data. This second embodiment of the invention further comprises a signal receiving and storage device and an image display system, as described for the first embodiment, above.

Figure 3:
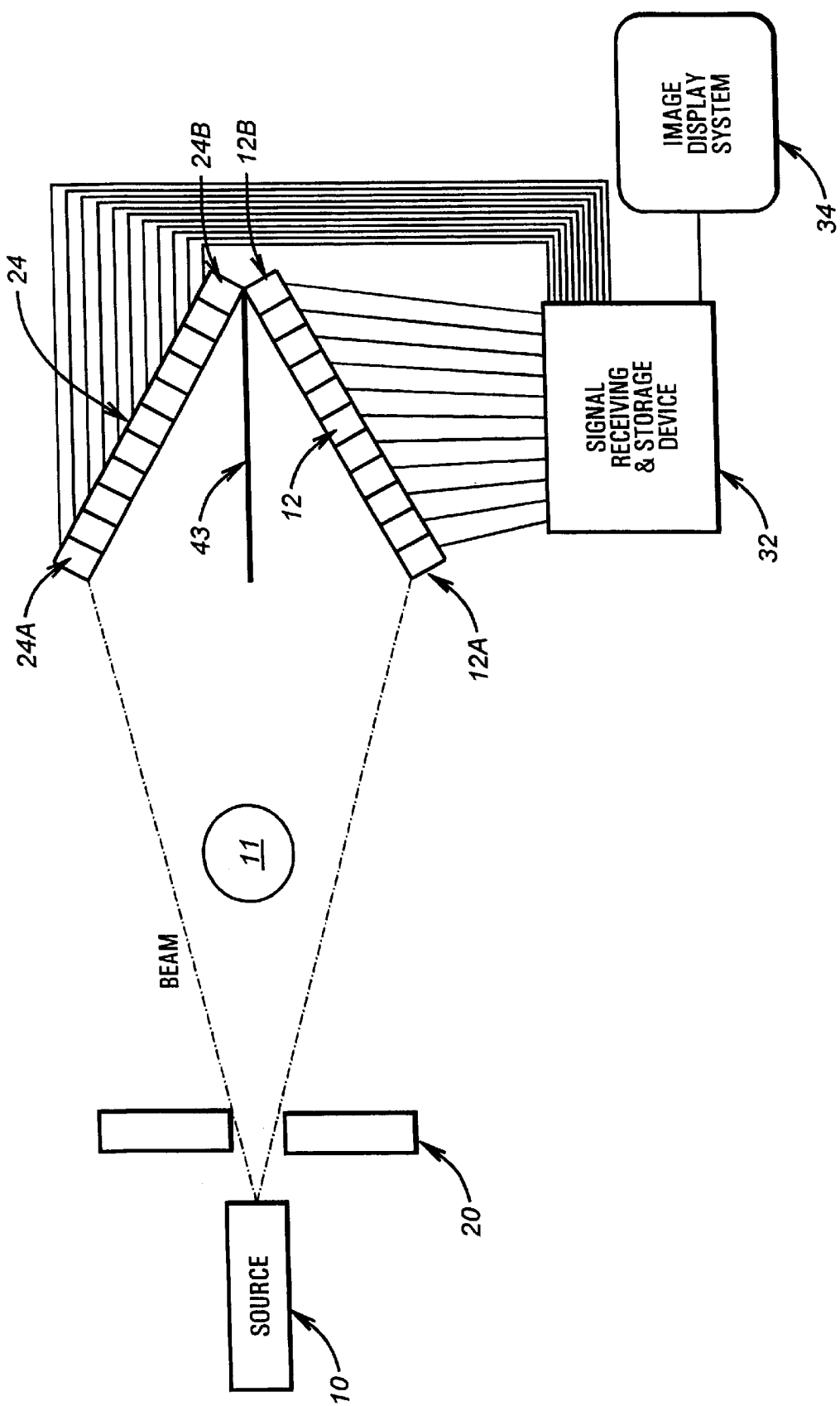
FIG. 3 is a top view of a third embodiment of the present invention.

A third embodiment of the present invention is shown in FIG. 3. This embodiment of the present invention comprises all of the elements depicted in FIG. 1 of the present invention. Additionally, this embodiment of the present invention comprises a second detector array 24 comprising a proximal end 24a and a distal end 24b. The proximal end of the second detector array is closer to the radiation source then the distal end.

The second detector array is capable of generating a signal indicative of integrated or counting data. The second detector array is positioned with respect to the first detector array such that the distal ends of the first and second arrays are substantially in contact and the proximal ends of the first and second arrays are spaced apart such that they form an opening approximately the same size as the radiation beam. The opening formed by the proximal ends of the first and second detector arrays face the radiation beam.

In a preferred embodiment of the invention, as shown in FIG. 2, each detector array comprises a multiplicity of cells 26 wherein each cell comprises a center and is placed against at least one other adjacent cell. In another preferred embodiment, the invention may also comprise a collimator, as shown in FIG. 3. The need or desirability of having a collimator is a function of the size of the target body. In general, the probability of needing a collimator is proportional to the size of the target.

In a preferred embodiment, the distal ends of the first and second arrays are spaced apart a distance that is less than or equal to 20% of the distance between the centers of adjacent cells within each detector array. In a preferred embodiment, each detector array comprises a continuous medium for detecting electromagnetic radiation 29.

Figure 10:
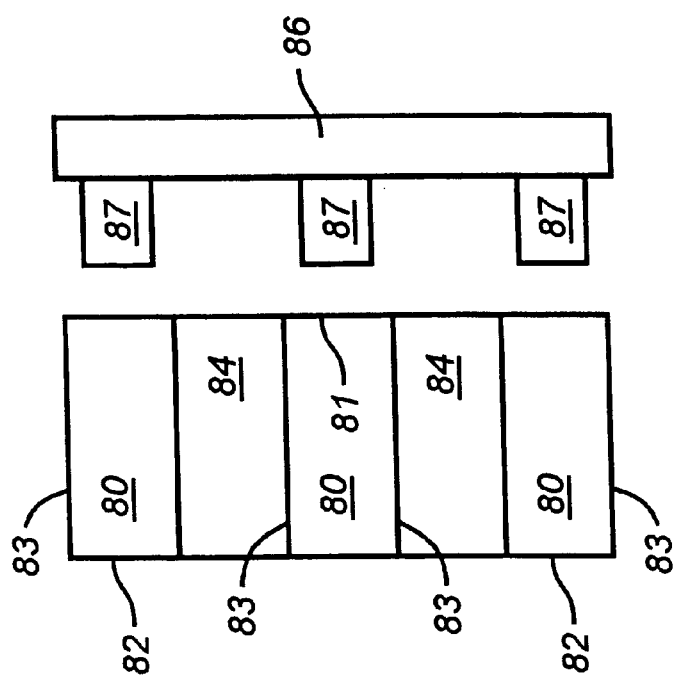
FIG. 10 is a top view of another detector array embodiment of the present invention.

Another preferred embodiment of a detector array of the present invention is shown in FIG. 10. In this embodiment, each detector array comprises a multiplicity of scintillation crystals 80. Each of said crystals has a first end 81 a second end 82 and two sides 83.

This detector array embodiment further comprises a spacer medium 84 positioned between the sides of the scintillation crystals. This medium has low x-ray absorbing and high light reflecting properties. The term "low x-ray absorbing", as used herein, means that less than approximately 20% of incident x-ray photons are absorbed in the material. The term "high light reflecting", as used herein, means that more than approximately 80% of the light photons produced in a crystal are reflected back into the crystal by the material.

This detector array embodiment further comprises a substrate 86 extending across the first end of the scintillation crystals. This embodiment further comprises a multiplicity of light sensitive elements 87 mounted on the substrate such that each element faces the first end of a respective crystal as shown in FIG. 10.

In a preferred embodiment, the spacer medium comprises magnesium oxide power suspended in a binder. In another preferred embodiment, the light sensitive elements are photodiodes.

In another preferred embodiment, the invention further comprises an x-ray absorbing septum 43 placed between the first and second detector arrays as shown in FIG. 3. In a preferred embodiment, the x-ray absorbing septum is a plate comprising tungsten.

Figure 8:
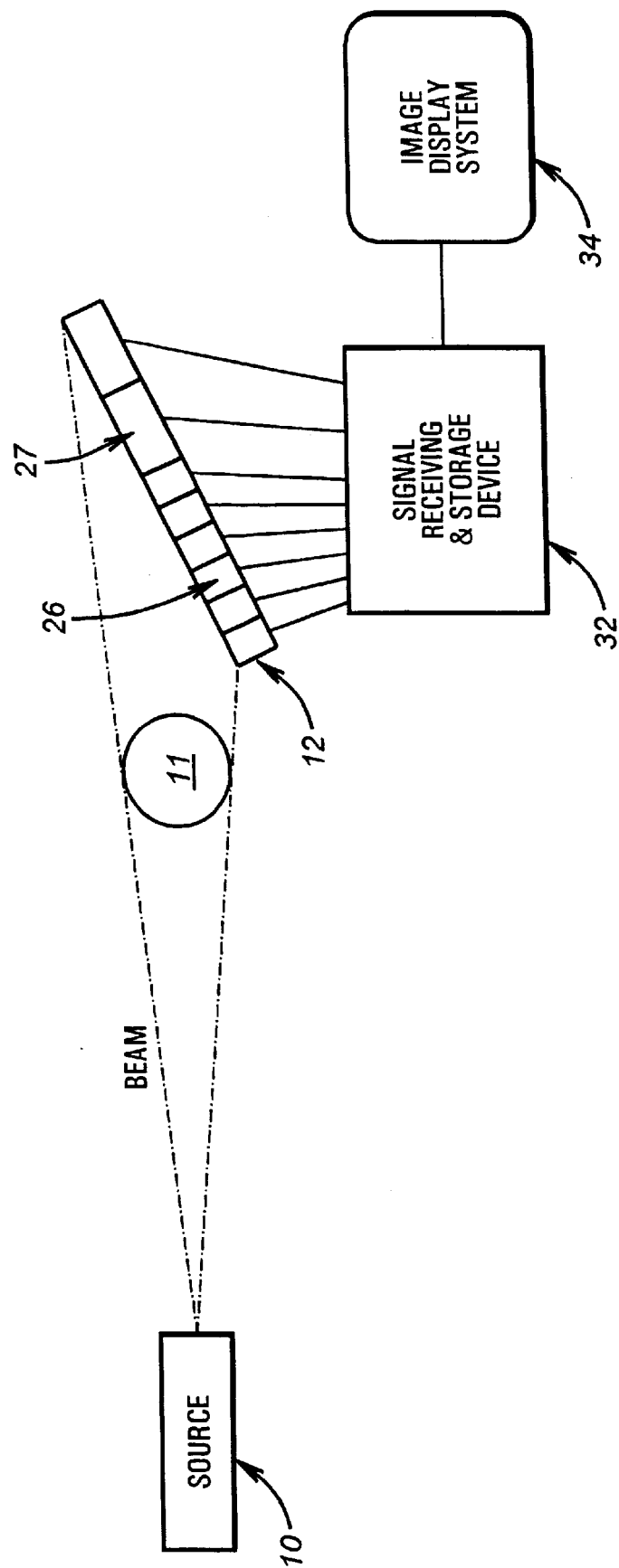
FIG. 8 is a top view of a detector array embodiment of the present invention.
Figure 9:
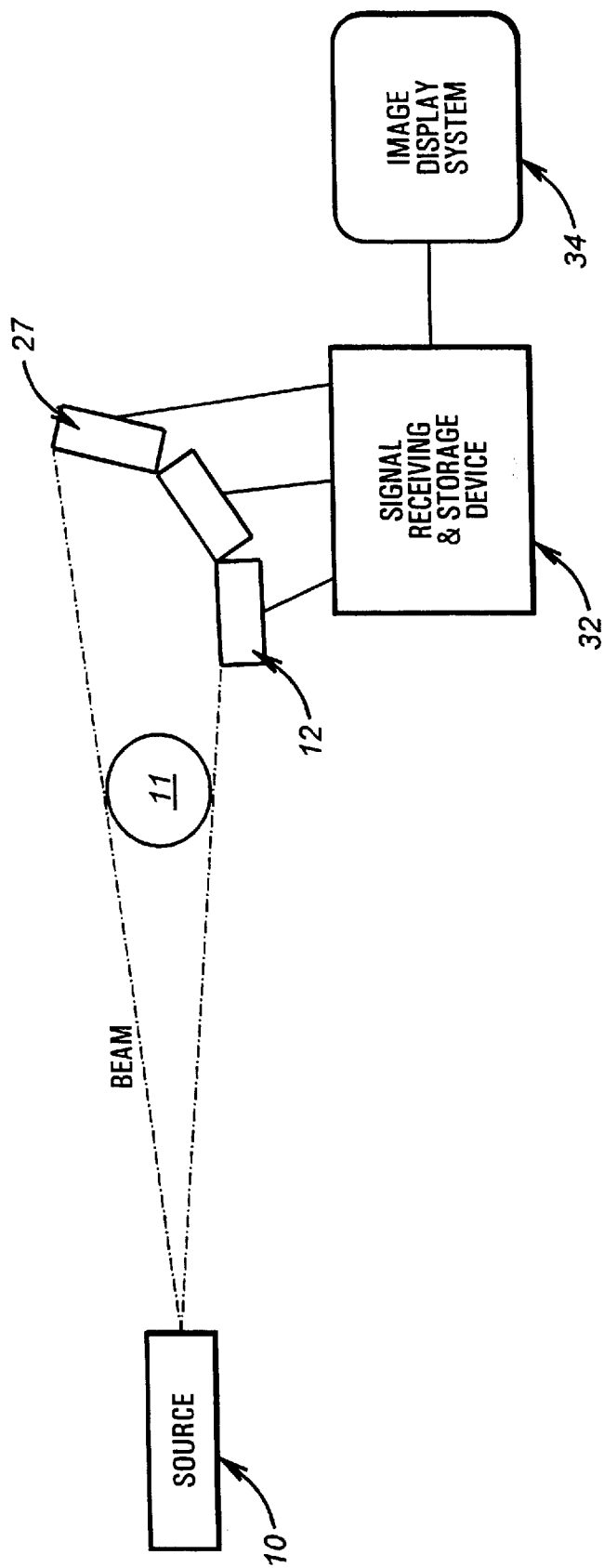
FIG. 9 is a top view of a detector array embodiment of the present invention.

In a preferred embodiment each detector array comprises at least two linear subarrays 27 each of which comprises a mulpiplicity of detector cells 26, as shown in FIG. 8. In a preferred embodiment, each subarray is positioned at an angle with respect to its adjacent subarray such that the first detector array is arranged in an arched configuration, as shown in FIG. 9.

Figure 4:
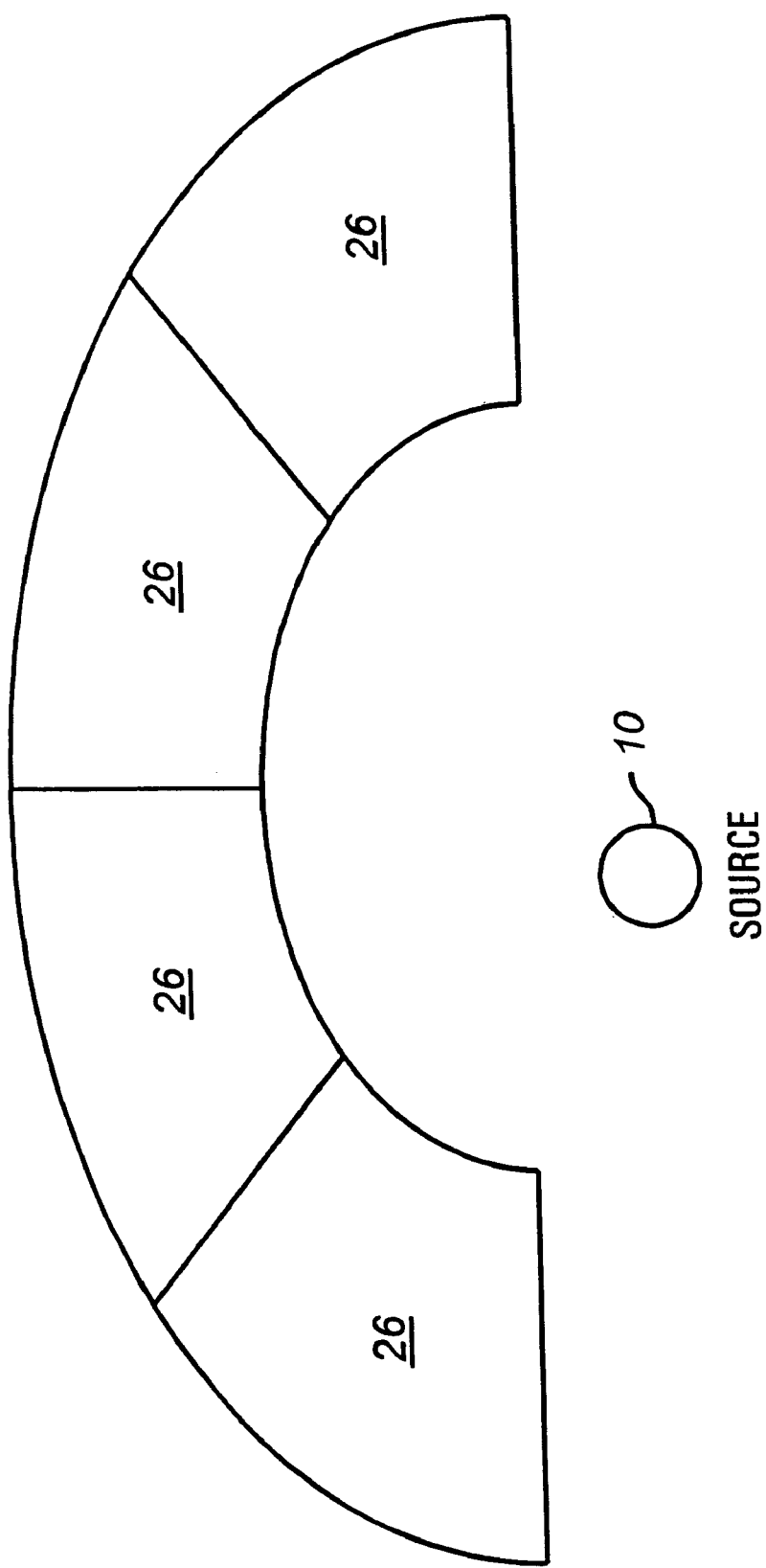
FIG. 4 is a top view of a first detector array embodiment of the present invention.
Figure 5:
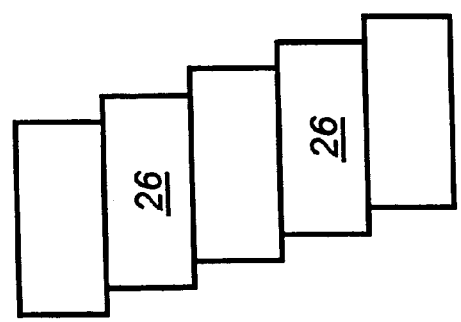
FIG. 5 is a top view of a second detector array embodiment of the present invention.

In a preferred embodiment, as shown in FIG. 4, the first detector array comprises a multiplicity of cells 26 arranged in an arcuate geometry. In a preferred embodiment, the cells are arranged in a stairstep configuration, as shown in FIG. 5. The first detector array is oriented such that the radiation beam strikes the array at an angle within a range of 0.0005–90 degrees.

In a preferred embodiment, each detector array comprises a multiplicity of cells arranged in an arcuate geometry, as described above. In a preferred embodiment, the cells are arranged in a stairstep configuration, as shown in FIG. 5.

The foregoing disclosure and description of the invention are illustrative and explanatory. Various changes in the size, shape, and materials, as well as in the details of the illustrative construction may be made without departing from the spirit of the invention.

What is claimed is:

1. An imaging system for providing an image of a target body, comprising:

a. a radiation source capable of emitting a beam of electromagnetic radiation, said source aimed at a target body;

b. a first detector array comprising a proximal end, a distal end, and a multiplicity of cells arranged in a stair stepped configuration, said proximal end being closer to said radiation source than said distal end, said first detector array being oriented such that said radiation beam strikes said detector array at an angle within the range of 0.0005–90 degrees, said first detector array being capable of generating signals indicative of integrated or counting data;

c. a signal receiving and storage device connected to receive signals indicative of integrated or counting data and to store integrated or counting data from said detector array;

d. an image display system coupled to said receiving and storage device and capable of displaying images derived from integrated or counting data stored in said device; and e. a collimator positioned between said radiation source and a target body so as to control the lateral dimension of said beam within a preselected range.

2. The system of claim 1, wherein said signal receiving and storage device further comprises an energy discriminating device and a multiplicity of bins such that said received signals can be stored according to their energy level.

3. The system of claim 2, wherein said energy discriminating device comprises a pulse height analyzer.

4. The system of claim 1, wherein the first detector array comprises a multiplicity of cells arranged in an arcuate geometry.

5. The system of claim 4, wherein each of said cells comprises a scintillator crystal and photomultiplier tube.

6. The system of claim 1, further comprising a rotatable gantry having a first side to which said radiation source and said collimator are affixed, and further having a second side to which said detector array is affixed.

7. The system of claim 6, further comprising an antiscatter collimator affixed to the second side of said gantry and positioned between said detector array and said radiation source.

8. The system of claim 1, wherein said first detector array comprises a multiplicity of cells, wherein each cell comprises a center and each cell is placed against at least one other adjacent cell.

9. The system of claim 1, wherein said first detector array comprises a continuous medium for detecting electromagnetic radiation.

10. The system of claim 1, wherein said first detector array comprises at least two linear subarrays, each of said subarrays comprising a multiplicity of detector cells.

11. The system of claim 10, wherein each of said subarrays is positioned at an angle with respect to its adjacent subarray such that the first detector array is arranged in an arched configuration.

12. The system of claim 1, wherein said first detector array comprises:
   a. a multiplicity of scintillation crystals, each of said crystals having a first end, a second end and two sides;
   b. a spacer medium positioned between the sides of said crystals, said medium having low x-ray absorbing, high light reflecting properties;
   c. a substrate extending across the first ends of said crystals; and
   d. a multiplicity of light sensitive elements mounted on said substrate such that each element faces the first end of a respective crystal.

13. The system of claim 12, wherein said medium comprises magnesium oxide powder suspended in a binder.

14. The system of claim 13, wherein said light sensitive elements are photodiodes.

15. An imaging system for providing an image of a target body, comprising:
   a. a radiation source capable of emitting a beam of electromagnetic radiation, said source aimed at a target body;
   b. a first detector array comprising a proximal end and a distal end, said proximal end being closer to said radiation source than said distal end, said detector array being oriented such that said radiation beam strikes said detector array at an angle within the range of 0.0005–90 degrees, said detector array being capable of generating a signal indicative of integrated or counting data;
   c. a second detector array comprising a proximal end and a distal end, said proximal end being closer to said radiation source than said distal end, said second detector array being capable of generating a signal indicative of integrated or counting data, said second detector array positioned with respect to said first detector array such that the distal ends of said first and second arrays are substantially in contact and the proximal ends of said first and second arrays are spaced apart such that they form an opening approximately the same size as said beam, said opening facing said beam, said second detector array being oriented such that said radiation beam strikes said second detector array at an angle within the range of 0.0005–90 degrees, said second detector array being capable of generating signals indicative of integrated of counting data;
   d. a signal receiving and storage device connected to receive one or more signals indicative of integrated or counting data from said detector arrays, and to store integrated or counting data from said detector arrays;
   e. an image display system coupled to said receiving and storage device and capable of displaying images derived from integrated or counting data stored in said device; and
   f. a collimator positioned between said radiation source and a target body so as to control the lateral size of said beam within a preselected range,
   g. wherein each of said first and second detector arrays comprises a multiplicity of cells arranged in a stair stepped configuration.

16. The system of claim 15, wherein each of said first and second detector arrays comprises a continuous medium for detecting electromagnetic radiation.

17. The system of claim 15, further comprising an X-ray absorbing septum placed between said first and second detector arrays.

18. The system of claim 17, wherein said septum is a plate comprising tungsten.

19. The system of claim 15, wherein said signal receiving and storage device further comprises an energy discriminating device and a multiplicity of bins such that said received signals can be stored according to their energy level.

20. The system of claim 19, wherein said energy discriminating device comprises a pulse height analyzer.

21. The system of claim 15, wherein at least one of said first and second detector arrays comprises:
   a. a multiplicity of scintillation crystals, each of said crystals having a first end, a second end and two sides;
   b. a spacer medium positioned between the sides of said crystals, said medium having low x-ray absorbing, high light reflecting properties;
   c. a substrate extending across the first ends of said crystals; and
   d. a multiplicity of light sensitive elements mounted on said substrate such that each element faces the first end of a respective crystal.

22. The system of claim 21, wherein said medium comprises magnesium oxide powder suspended in a binder.

23. The system of claim 22, wherein said light sensitive elements are photodiodes.

24. The system of claim 15, wherein each of said first and second detector arrays comprises a multiplicity of cells, wherein each cell comprises a center and each cell is placed against at least one other adjacent cell.

25. The system of claim 24, wherein each of said first and second detector arrays comprises a multiplicity of cells arranged in an arcuate geometry.

26. The system of claim 24, wherein each of said cells comprises a scintillator crystal and photomultiplier tube.

27. The system of claim 24, wherein the distal ends of said first and second arrays are spaced apart a distance that is less than or equal to 20% of the distance between the centers of said adjacent cells within each detector array.

28. The system of claim 27, further comprising a rotatable gantry having a first side to which said radiation source and said collimator are affixed, and further having a second side to which one of said first and second detector arrays is affixed.

29. The system of claim 28, further comprising an anti-scatter collimator affixed to the second side of said gantry and positioned between one of said first and second detector arrays and said radiation source.

30. The system of claim 27, wherein at least one of said first and second detector arrays comprises at least two linear subarrays, each of said subarrays comprising a multiplicity of detector cells.

31. The system of claim 30, wherein each of said subarrays is positioned at an angle with respect to its adjacent subarray such that the first detector array is arranged in an arched configuration.

* * * * *

UNITED STATES PATENT AND TRADEMARK OFFICE
CERTIFICATE OF CORRECTION

PATENT NO. : 6,335,957 B1
DATED : January 1, 2002
INVENTOR(S) : DiBianca

It is certified that error appears in the above-identified patent and that said Letters Patent is hereby corrected as shown below:

<u>Title page,</u>
Item [73], Assignee, please change "The University of Tennessee Research Center, Knoxville, TN (US)" to -- The University of Tennessee Research Corporation, Knoxville, TN (US) --

Signed and Sealed this

Tenth Day of September, 2002

Attest:

Attesting Officer

JAMES E. ROGAN
*Director of the United States Patent and Trademark Office*